United States Patent
Pursell et al.

(10) Patent No.: US 11,634,715 B2
(45) Date of Patent: Apr. 25, 2023

(54) METHODS AND COMPOSITIONS FOR TREATING BILE DUCT PAUCITY-ASSOCIATED CONDITIONS

(71) Applicant: Dicerna Pharmaceuticals, Inc., Lexington, MA (US)

(72) Inventors: Natalie Pursell, Westborough, MA (US); Cheng Lai, Hudson, NH (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 153 days.

(21) Appl. No.: 16/975,946

(22) PCT Filed: Feb. 15, 2019

(86) PCT No.: PCT/US2019/018184
§ 371 (c)(1),
(2) Date: Aug. 26, 2020

(87) PCT Pub. No.: WO2019/168686
PCT Pub. Date: Sep. 6, 2019

(65) Prior Publication Data
US 2021/0010005 A1  Jan. 14, 2021

Related U.S. Application Data

(60) Provisional application No. 62/637,973, filed on Mar. 2, 2018.

(51) Int. Cl.
*C12N 15/113* (2010.01)
*A61P 1/16* (2006.01)

(52) U.S. Cl.
CPC ............ *C12N 15/1135* (2013.01); *A61P 1/16* (2018.01)

(58) Field of Classification Search
CPC .............................. C12N 15/1135; A61P 1/16
See application file for complete search history.

(56) References Cited

U.S. PATENT DOCUMENTS

| | | |
|---|---|---|
| 8,815,825 B2 | 8/2014 | Brown et al. |
| 9,243,244 B2 | 1/2016 | Brown et al. |
| 9,428,752 B2 | 8/2016 | Brown et al. |
| 10,072,263 B2 | 9/2018 | Brown et al. |
| 10,612,023 B2 | 4/2020 | Brown et al. |
| 2013/0109740 A1 | 5/2013 | Brown et al. |
| 2014/0079680 A1 | 3/2014 | Alpini et al. |
| 2017/0275626 A1* | 9/2017 | Maier ............. A61P 43/00 |

FOREIGN PATENT DOCUMENTS

| | | | |
|---|---|---|---|
| WO | 2012006243 A2 | 1/2012 | |
| WO | 2012135848 A2 | 10/2012 | |
| WO | WO-2016057932 A1 * | 4/2016 | ........ A61K 31/713 |
| WO | 2019168686 A1 | 9/2019 | |

OTHER PUBLICATIONS

Boulter et al., "WNT signaling drives cholangiocarcinoma growth and can be pharmacologically inhibited," J Clin Invest. 2015; 125(3):1269-85.
Delgado et al., "Complete response of Ctnnb1-mutated tumours to β-catenin suppression by locked nucleic acid antisense in a mouse hepatocarcinogenesis model," J Hepatol. 2015; 62(2):380-7.
International Search Report and Written Opinion issued in International Application No. PCT/US2019/018184, dated May 14, 2019 (12 pages).
Shen at al., "Inhibition of Wnt/β-catenin signaling downregulates P-glycoprotein and reverses multi-drug resistance of cholangiocarcinoma," Cancer Sci. 2013; 104(10):1303-8.
Dicerna, "Welcome to Investor Day," Jun. 29, 2016; https://investors.dicerna.com/static-files/ee0ae41f-ca11-4c01-889f-d3493ff71a55. Accessed Dec. 16, 2021.
Mariotti et al., "Animal models of biliary injury and altered bile acid metabolism," Biochim Biophys Acta Mol Basis Dis. Apr. 2018;1864(4 Pt B):1254-1261.
Thompson et al., "ß-Catenin regulation of farnesoid X receptor signaling and bile acid metabolism during murine cholestasis," Hepatology. Mar. 2018;67(3):955-71.

* cited by examiner

*Primary Examiner* — J. E. Angell
(74) *Attorney, Agent, or Firm* — Dechert LLP; Andrea L. C. Reid; Gang Wang

(57) ABSTRACT

This disclosure relates to oligonucleotides, compositions and methods useful for reducing CTNNB1 expression, particularly in hepatocytes, for the treatment of bile duct paucity-associated conditions. Disclosed oligonucleotides for the reduction of CTNNB1 expression may be double-stranded or single-stranded, and may be modified for improved characteristics such as stronger resistance to nucleases and lower immunogenicity. Disclosed oligonucleotides for the reduction of CTNNB1 expression may also include targeting ligands to target a particular cell or organ, such as the hepatocytes of the liver.

22 Claims, 8 Drawing Sheets
Specification includes a Sequence Listing.

```
                         SEQUENCE LISTING

<160> NUMBER OF SEQ ID NOS: 3

<210> SEQ ID NO 1
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 1
cgaggaguaa caaucaaaa gcagccgaaa ggcugc                                  36

<210> SEQ ID NO 2
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 2
uuuuguauug uuacuccucg gg                                                22

<210> SEQ ID NO 3
<211> LENGTH: 3720
<212> TYPE: DNA
<213> ORGANISM: Homo sapiens

<400> SEQUENCE: 3
aggatacagc ggcttctgcg cgacttataa gagctccttg tgcggcgcca ttttaagcct       60
ctcggtctgt ggcagcagcg ttggcccggc cccgggagcg gagagcgagg ggaggcggag      120
acggaggaag gtctgaggag cagcttcagt ccccgccgag ccgccaccgc aggtcgagga      180
cggtcggact cccgcggcgg gaggagcctg ttcccctgag ggtatttgaa gtataccata      240
caactgtttt gaaaatccag cgtggacaat ggctactcaa gctgatttga tggagttgga      300
catggccatg gaaccagaca gaaaagcggc tgttagtcac tggcagcaac agtcttacct      360
ggactctgga atccattctg gtgccactac cacagctcct tctctgagtg gtaaaggcaa      420
tcctgaggaa gaggatgtgg atacctccca agtcctgtat gagtgggaac agggattttc      480
tcagtccttc actcaagaac aagtagctga tattgatgga cagtatgcaa tgactcgagc      540
tcagagggta cgagctgcta tgttccctga gacattagat gagggcatgc agatcccatc      600
tacacagttt gatgctgctc atcccactaa tgtccagcgt ttggctgaac catcacagat      660
gctgaaacat gcagttgtaa acttgattaa ctatcaagat gatgcagaac ttgccacacg      720
tgcaatccct gaactgacaa aactgctaaa tgacgaggac caggtggtgg ttaataaggc      780
tgcagttatg gtccatcagc tttctaaaaa ggaagcttcc agacacgcta tcatgcgttc      840
tcctcagatg gtgtctgcta ttgtacgtac catgcagaat acaaatgatg tagaaacagc      900
tcgttgtacc gctgggacct tgcataacct ttcccatcat cgtgagggct tactggccat      960
ctttaagtct ggaggcattc ctgccctggt gaaaatgctt ggttcaccag tggattctgt     1020
gttgttttat gccattacaa ctctccacaa ccttttatta catcaagaag gagctaaaat     1080
ggcagtgcgt ttagctggtg ggctgcagaa aatggttgcc ttgctcaaca aaacaaatgt     1140
taaattcttg gctattacga cagactgcct tcaaattta gcttatggca accaagaaag     1200
```

```
caagctcatc atactggcta gtggtggacc ccaagcttta gtaaatataa tgaggaccta    1260
tacttacgaa aaactactgt ggaccacaag cagagtgctg aaggtgctat ctgtctgctc    1320
tagtaataag ccggctattg tagaagctgg tggaatgcaa gctttaggac ttcacctgac    1380
agatccaagt caacgtcttg ttcagaactg tctttggact ctcaggaatc tttcagatgc    1440
tgcaactaaa caggaaggga tggaaggtct ccttgggact cttgttcagc ttctgggttc    1500
agatgatata aatgtggtca cctgtgcagc tggaattctt tctaacctca cttgcaataa    1560
ttataagaac aagatgatgg tctgccaagt gggtggtata gaggctcttg tgcgtactgt    1620
ccttcgggct ggtgacaggg aagacatcac tgagcctgcc atctgtgctc ttcgtcatct    1680
gaccagccga caccaagaag cagagatggc ccagaatgca gttcgccttc actatggact    1740
accagttgtg gttaagctct tacacccacc atcccactgg cctctgataa aggctactgt    1800
tggattgatt cgaaatcttg ccctttgtcc cgcaaatcat gcacctttgc gtgagcaggg    1860
tgccattcca cgactagttc agttgcttgt tcgtgcacat caggataccc agcgccgtac    1920
gtccatgggt gggacacagc agcaatttgt ggagggggtc cgcatggaag aaatagttga    1980
aggttgtacc ggagcccttc acatcctagc tcgggatgtt cacaaccgaa ttgttatcag    2040
aggactaaat accattccat tgtttgtgca gctgctttat tctcccattg aaaacatcca    2100
aagagtagct gcaggggtcc tctgtgaact tgctcaggac aaggaagctg cagaagctat    2160
tgaagctgag ggaccacag ctcctctgac agagttactt cactctagga atgaaggtgt    2220
ggcgacatat gcagctgctg ttttgttccg aatgtctgag acaagccac aagattacaa    2280
gaaacggctt tcagttgagc tgaccagctc tctcttcaga acagagccaa tggcttggaa    2340
tgagactgct gatcttggac ttgatattgg tgcccaggga gaaccccttg gatatcgcca    2400
ggatgatcct agctatcgtt cttttcactc tggtggatat ggccaggatg ccttgggtat    2460
ggaccccatg atggaacatg agatgggtgg ccaccaccct ggtgctgact atccagttga    2520
tgggctgcca gatctgggc atgcccagga cctcatggat gggctgcctc caggtgacag    2580
caatcagctg gcctggtttg atactgacct gtaaatcatc ctttaggtaa aagtttta    2640
aaagccagtt tgggtaaaat acttttactc tgcctacaga acttcagaaa gacttggttg    2700
gtagggtggg agtggtttag gctatttgta aatctgccac aaaaacaggt atatactttg    2760
aaaggagatg tcttggaaca ttggaatgtt ctcagatttc tggttgttat gtgatcatgt    2820
gtggaagtta ttaactttaa tgtttttgc cacagctttt gcaacttaat actcaaatga    2880
gtaacatttg ctgttttaaa cattaatagc agcctttctc tctttataca gctgtattgt    2940
ctgaacttgc attgtgattg gcctgtagag ttgctgagag ggctcgaggg gtgggctggt    3000
atctcagaaa gtgcctgaca cactaaccaa gctgagtttc ctatgggaac aattgaagta    3060
aactttttgt tctggtcctt tttggtcgag gagtaacaat acaaatggat tttgggagtg    3120
actcaagaag tgaagaatgc acaagaatgg atcacaagat ggaattatc aaaccctagc    3180
cttgcttgtt aaattttttt tttttttttt ttaagaatat ctgtaatggt actgactttg    3240
cttgctttga agtagctctt ttttttttt tttttttttt tttgcagtaa ctgtttttta    3300
agtctctcgt agtgttaagt tatagtgaat actgctacag caatttctaa ttttaagaa    3360
ttgagtaatg gtgtagaaca ctaattcata atcactctaa ttaattgtaa tctgaataaa    3420
gtgtaacaat tgtgtagcct ttttgtataa aatagacaaa tagaaaatgg tccaattagt    3480
ttcctttta atatgcttaa aataagcagg tggatctatt tcatgttttt gatcaaaaac    3540
tatttgggat atgtatgggt agggtaaatc agtaagaggt gttatttgga accttgtttt    3600
```

```
ggacagttta ccagttgcct tttatcccaa agttgttgta acctgctgtg atacgatgct    3660
tcaagagaaa atgcggttat aaaaaatggt tcagaattaa acttttaatt cattcgattg    3720
```

METHODS AND COMPOSITIONS FOR TREATING BILE DUCT PAUCITY-ASSOCIATED CONDITIONS

CROSS REFERENCE TO RELATED APPLICATIONS

This application is a National Stage application, filed under 35 U.S.C. § 371, of International Application No. PCT/US2019/018184, filed Feb. 15, 2019, which claims the benefit under 35 U.S.C. § 119(e) to U.S. Provisional Application No. 62/637,973, filed Mar. 2, 2018, and entitled "METHODS AND COMPOSITIONS FOR TREATING BILE DUCT PAUCITY-ASSOCIATED CONDITIONS," the entire contents of each of which are incorporated herein by reference.

FIELD OF THE INVENTION

The present application relates to oligonucleotides and uses thereof, particularly uses relating to the treatment of conditions relating to bile duct paucity.

REFERENCE TO THE SEQUENCE LISTING

The present application is being filed along with a Sequence Listing in electronic format. The Sequence Listing is provided as a file entitled D0800.70013WO00—SEQ.txt created on Feb. 15, 2019 which is 5.45 KB in size. The information in electronic format of the sequence listing is incorporated herein by reference in its entirety.

BACKGROUND OF THE INVENTION

Disorders affecting bile acid production, secretion and/or uptake can have significant physiological implications. For example, cholestasis is a common liver disease, particularly in neonates, which results in diminished bile flow and excretion, and prolonged conjugated hyperbilirubinemia. Similarly, paucity of intrahepatic bile ducts is associated with various disorders and anomalies, including the familial syndrome, referred to as Alagille syndrome (AGS), which involves chronic cholestasis, cardiac anomalies, musculoskeletal abnormalities, ocular anomalies, and dysmorphic faces. In many individuals, particularly those suffering from AGS, paucity of bile ducts is associated with rapidly progressive liver disease. Biliary Atresia (BA) is another progressive, fibro-obliterative disorder of the intra- and extrahepatic bile ducts in infancy. Suitable methods for treating such patients, including methods for improving bile duct paucity, are lacking.

BRIEF SUMMARY OF THE INVENTION

Aspects of the disclosure relate to methods for treating bile duct paucity and related conditions in a subject. In some embodiments, the disclosure relates to the discovery that selectively inhibiting CTNNB1 expression in a subject is useful for increasing bile duct capacity (e.g., for stimulating new bile duct formation) of the subject. In some embodiments, methods provided herein utilize RNAi oligonucleotides for reducing β-catenin activity in a subject, and thereby increasing bile duct capacity (e.g., promoting regeneration of bile ducts) of the subject. A consequence of the increased bile duct capacity produced by methods provided herein is an improvement in bile flow (e.g., increased bile acid uptake) and a corresponding decrease in circulating bile acid (see, e.g., Example 4, which shows that administration of CTNNB1 RNAi oligonucleotides reduced bile acid levels in an animal model of bile duct damage). In some embodiments, reduction of β-catenin activity decreases bile acid synthesis in hepatocytes, which can prevent bile acid-induced acute toxicity due to bile duct paucity in a subject. Accordingly, in some embodiments, methods provided herein are useful for treating bile duct paucity-associated conditions, such as Alagille syndrome and Biliary Atresia through regeneration of new bile ducts and reduction of bile acid synthesis.

One aspect of the present disclosure provides oligonucleotides for reducing expression of CTNNB1, in which the oligonucleotides comprise an antisense strand of 15 to 30 nucleotides in length. In some embodiments, the region of complementarity is at least 15, at least 16, at least 17, at least 18, at least 19, at least 20, at least 21, or at least 22 contiguous nucleotides in length. In some embodiments, the region of complementarity is fully complementary to the target sequence of CTNNB1. In some embodiments, the region of complementarity to CTNNB1 is at least 19 contiguous nucleotides in length.

In some embodiments, the antisense strand is 19 to 27 nucleotides in length. In some embodiments, the antisense strand is 21 to 27 nucleotides in length. In some embodiments, the oligonucleotide further comprises a sense strand of 15 to 40 nucleotides in length, in which the sense strand forms a duplex region with the antisense strand. In some embodiments, the sense strand is 19 to 40 nucleotides in length. In some embodiments, the antisense strand is 27 nucleotides in length and the sense strand is 25 nucleotides in length. In some embodiments, the duplex region is at least 15, at least 16, at least 17, at least 18, at least 19, at least 20, or at least 21 nucleotides in length. In some embodiments, the antisense strand and sense strand form a duplex region of 25 nucleotides in length.

In some embodiments, an oligonucleotide further comprises a 3'-overhang sequence on the antisense strand of two nucleotides in length. In some embodiments, an oligonucleotide comprises an antisense strand and a sense strand that are each in a range of 21 to 23 nucleotides in length. In some embodiments, an oligonucleotide comprises a duplex structure in a range of 19 to 21 nucleotides in length. In some embodiments, an oligonucleotide comprises a 3'-overhang sequence of one or more nucleotides in length, in which the 3'-overhang sequence is present on the antisense strand, the sense strand, or the antisense strand and sense strand. In some embodiments, an oligonucleotide comprises a 3'-overhang sequence of two nucleotides in length, in which the 3'-overhang sequence is present on the antisense strand, and in which the sense strand is 21 nucleotides in length and the antisense strand is 23 nucleotides in length, such that the sense strand and antisense strand form a duplex of 21 nucleotides in length.

In some embodiments, the region of complementarity to CTNNB1 is at least 19 contiguous nucleotides in length. In some embodiments, the sense strand comprises at its 3'-end a stem-loop set forth as: S1-L-S2, in which S1 is complementary to S2, and in which L forms a loop between S1 and S2 of 3 to 5 nucleotides in length.

Another aspect of the present disclosure provides an oligonucleotide for reducing expression of CTNNB1, the oligonucleotide comprising an antisense strand and a sense strand, in which the antisense strand is 21 to 27 nucleotides in length and has a region of complementarity to CTNNB1, in which the sense strand comprises at its 3'-end a stem-loop set forth as: S1-L-S2, in which S1 is complementary to S2, and in which L forms a loop between S1 and S2 of 3 to 5 nucleotides in length, and in which the antisense strand and the sense strand form a duplex structure of at least 19 nucleotides in length but are not covalently linked. In some embodiments, the region of complementarity is fully complementary to at least 15, at least 16, at least 17, at least 18, at least 19, at least 20, or at least 21 contiguous nucleotides of CTNNB1 mRNA. In some embodiments, L is a tetraloop. In some embodiments, L is 4 nucleotides in length. In some embodiments, L comprises a sequence set forth as GAAA.

In some embodiments, an oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of an oligonucleotide are modified.

In some embodiments, an oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate.

In some embodiments, at least one nucleotide of an oligonucleotide is conjugated to one or more targeting ligands. In some embodiments, each targeting ligand comprises a carbohydrate, amino sugar, cholesterol, polypeptide or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety. In some embodiments, the targeting ligand comprises an aptamer.

Another aspect of the present disclosure provides a composition comprising an oligonucleotide of the present disclosure and an excipient. Another aspect of the present disclosure provides a method comprising administering a composition of the present disclosure to a subject. In some embodiments, the method results in decreased bile duct paucity in a subject. In some embodiments, the method results in an increase in bile duct formation, and thus an increase in bile duct capacity, in a subject. In some embodiments, the subject to be treated suffers from Alagille syndrome. In some embodiments, the subject to be treated suffers from Biliary Atresia.

Another aspect of the present disclosure provides an oligonucleotide for reducing expression of CTNNB1, the oligonucleotide comprising a sense strand of 15 to 40 nucleotides in length and an antisense strand of 15 to 30 nucleotides in length, in which the sense strand forms a duplex region with the antisense strand, and the antisense strand comprises a complementary sequence.

In some embodiments, the oligonucleotide comprises a pair of sense and antisense strands selected from a row of the table set forth in Appendix A.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

DETAILED DESCRIPTION OF THE INVENTION

Figure 1:
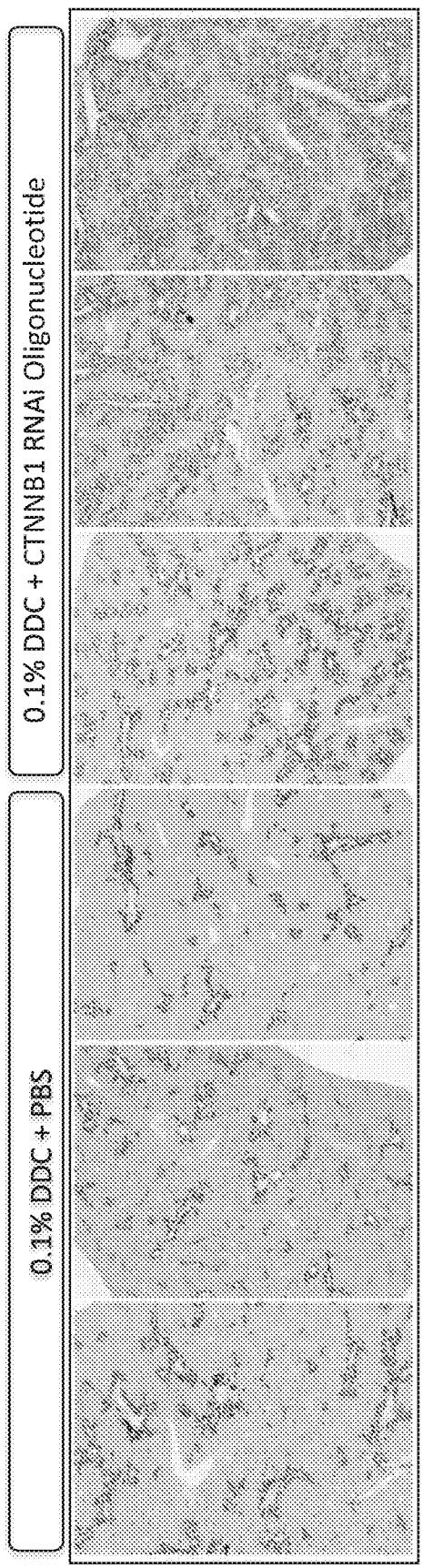
FIG. 1 is a series of photographs showing immunohistochemistry staining for CK19 in liver sections from mice fed with 0.1% 3,5-diethoxycarbonyl-1,4-dihydrocollidine (DDC) and treated with PBS (first three panels) and from mice fed with 0.1% DDC and treated with CTNNB1 RNAi oligonucleotide (last three panels). CK19 is a ductal epithelial marker. The CTNNB1 RNAi oligonucleotide is provided that comprises a sense strand having a sequence as set forth SEQ ID NO: 1 and an antisense strand having a sequence as set forth SEQ ID NO: 2.

According to some aspects, the disclosure provides methods utilizing oligonucleotides targeting CTNNB1 mRNA that are effective for reducing CTNNB1 expression in cells, particularly liver cells (e.g., hepatocytes) for the treatment of bile duct paucity. Accordingly, in related aspects, the disclosure provided methods of treating bile duct paucity that involve selectively reducing CTNNB1 gene expression in liver. In certain embodiments, CTNNB1 targeting oligonucleotides provided herein are designed for delivery to selected cells of target tissues (e.g., liver hepatocytes) to treat bile duct paucity in a subject.

Further aspects of the disclosure, including a description of defined terms, are provided below.

I. Definitions

Administering: As used herein, the terms "administering" or "administration" means to provide a substance (e.g., an oligonucleotide) to a subject in a manner that is pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Alagille syndrome: As used herein, "Alagille syndrome" refers to an disorder characterized by a narrowing, malformation, and/or paucity of bile ducts in the liver. In Alagille syndrome, impaired differentiation of intrahepatic bile ducts can lead to narrowing, malformation, and paucity of bile ducts. Such bile duct abnormalities reduce bile flow (intrahepatic cholestasis), resulting in a build-up of bile in the liver. See, e.g., Turnpenny et al. Alagille syndrome: pathogenesis, diagnosis and management. Eur J Hum Genet. 2012 March; 20(3):251-7, which is hereby incorporated by reference in its entirety for this purpose.

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

CTNNB1: As used herein, CTNNB1 is a gene that encodes β-catenin protein. In humans, CTNNB1 encodes at least four transcripts, namely NM_001904.3 (variant 1), NM_001098209.1 (variant 2), NM_001098210.1 (variant 3), and NM_001330729.1 (variant 4). Variants 1, 2, and 3 encode the same isoform (NP_001091680.1, isoform 1). Variant 4 encodes isoform 2 (NP_001317658.1), which has a shorter N-terminus compared to isoform 1. In mice, CTNNB1 encodes at least two transcripts, namely NM_007614.3 (variant 1) and NM_001165902.1 (variant 2). Both transcripts encode the same protein (see, e.g., sequences provided in NP_001159374.1 and NP_031640.1).

Bile duct paucity: As used herein, "bile duct paucity" refers to a diminished bile duct function resulting from an absence of bile ducts, a reduction in the number and/or size of bile ducts, or a blockage of bile ducts in a subject. In some embodiments, bile duct paucity is associated with an absence or reduced number of intrahepatic ducts. In some embodiments, bile duct paucity is associated with absence or reduced number of extrahepatic ducts. In some embodiments, bile duct paucity is associated with blockage of intrahepatic or extrahepatic ducts. As a non-limiting example, paucity of interlobular bile ducts may be calculated by determining the ratio of portal tracts lacking a bile duct compared to the total number of portal tracts (see, e.g., Hadchouel Paucity of interlobular bile ducts. Semin Diagn Pathol. 1992 February; 9(1):24-30, which is hereby incorporated by reference in its entirety for this purpose).

Bile duct paucity-associated condition: As used herein, the term "bile duct paucity-associated condition" or "BDP-associated condition" refers to a condition in a subject resulting in or associated with a reduction in the number or size of functional bile ducts in a subject compared with a normal control subject who does not have the condition. In some embodiments, a subject having a BDP-associated conditions has a reduction in the number and/or size of a functional bile ducts. In some embodiments, the defective biliary system in the subject occurs in intrahepatic bile ducts. In some embodiments, the intrahepatic ducts with impaired function are selected from the group consisting of: periportal bile ductules (canals of Hering), and intralobular bile ductules (cholangioles). In some embodiments, the bile ducts with impaired function in the subject are extrahepatic bile ducts. In some embodiments, the extrahepatic ducts with impaired function are selected from the group consisting of: the left hepatic duct, the right hepatic duct, and the common hepatic duct. In some embodiments, the BDP-associated condition is Alagille syndrome. In some embodiments, the BDP-associated condition is Biliary Atresia.

Biliary Atresia: As used herein, "Biliary Atresia (BA)" refers to a disease, particularly in infants, in which destruction or obliteration of bile ducts obstructs bile flow. See, e.g., Kelly et al. Current management of Biliary Atresia. Arch Dis Child. 2007 December; 92(12):1132-5, which is hereby incorporated by reference in its entirety for this purpose.

Complementary: As used herein, the term "complementary" refers to a structural relationship between nucleotides (e.g., two nucleotide on opposing nucleic acids or on opposing regions of a single nucleic acid strand) that permits the nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have nucleotide sequences that are complementary to each other so as to form regions of complementarity, as described herein.

Deoxyribonucleotide: As used herein, the term "deoxyribonucleotide" refers to a nucleotide having a hydrogen at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base-pairing of two antiparallel sequences of nucleotides.

Excipient: As used herein, the term "excipient" refers to a non-therapeutic agent that may be included in a composition, for example, to provide or contribute to a desired consistency or stabilizing effect.

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glul), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Loop: As used herein, the term "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to an internucleotide linkage having one or more chemical modifications compared with a reference internucleotide linkage comprising a phosphodiester bond. In some embodiments, a modified nucleotide is a non-naturally occurring linkage Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modifications in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc. In certain embodiments, a modified nucleotide comprises a 2'-O-methyl or a 2'-F substitution at the 2' position of the ribose ring.

Nicked Tetraloop Structure: A "nicked tetraloop structure" is a structure of a RNAi oligonucleotide characterized by the presence of separate sense (passenger) and antisense (guide) strands, in which the sense strand has a region of complementarity to the antisense strand such that the two strands form a duplex, and in which at least one of the strands, generally the sense strand, extends from the duplex in which the extension contains a tetraloop and two self-complementary sequences forming a stem region adjacent to the tetraloop, in which the tetraloop is configured to stabilize the adjacent stem region formed by the self-complementary sequences of the at least one strand.

Oligonucleotide: As used herein, the term "oligonucleotide" refers to a short nucleic acid, e.g., of less than 100 nucleotides in length. An oligonucleotide can comprise ribonucleotides, deoxyribonucleotides, and/or modified nucleotides including, for example, modified ribonucleotides. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base-pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotide.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, International Patent Application PCT/US2017/049909, filed on Sep. 1, 2017, U.S. Provisional Application Nos. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to CTNNB1 mRNA sequence) may result in a decrease in the amount of RNA transcript, protein and/or enzymatic activity (e.g., encoded by the CTNNB1 gene) compared to a cell that is not treated with the double-stranded oligonucleotide. Similarly, "reducing expression" as used herein refers to an act that results in reduced expression of a gene (e.g., CTNNB1).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides (e.g., a target nucleotide sequence within an mRNA) to permit hybridization between the two sequences of nucleotides under appropriate hybridization conditions, e.g., in a phosphate buffer, in a cell, etc. A region of complementarity may be fully complementary to a nucleotide sequence (e.g., a target nucleotide sequence present within an mRNA or portion thereof). For example, a region of complementarity that is fully complementary to a nucleotide sequence present in an mRNA has a contiguous sequence of nucleotides that is complementary, without any mismatches or gaps, to a corresponding sequence in the mRNA. Alternatively, a region of complementarity may be partially complementary to a nucleotide sequence (e.g., a nucleotide sequence present in an mRNA or portion thereof). For example, a region of complementary that is partially complementary to a nucleotide sequence present in an mRNA has a contiguous sequence of nucleotides that is complementary to a corresponding sequence in the mRNA but that contains one or more mismatches or gaps (e.g., 1, 2, 3, or more mismatches or gaps) compared with the corresponding sequence in the mRNA, provided that the region of complementarity remains capable of hybridizing with the mRNA under appropriate hybridization conditions.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject." In some embodiments, the subject is an adolescent human subject (e.g., less than 18 years of age, less than 12 years of age, less than 6 years of age, less than 3 years of age). However, in some embodiments, the subject is an adult human subject (e.g., of 18 or more years or age).

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature (Tm) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C. or at least 75° C. in 10 mM $NaHPO_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include but are not limited to non-Watson-Crick base-pairing, stacking interactions, hydrogen bonding, and contact interactions (Cheong et al., Nature 1990 Aug. 16;

346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors i. CTNNB1 Targeting Oligonucleotides

CTNNB1 targeting oligonucleotides can be used to achieve therapeutic benefit for subjects with bile duct paucity by reducing β-catenin activity, and consequently, by increasing bile duct formation and inhibiting bile acid synthesis. Any suitable CTNNB1 targeting oligonucleotide made be used. For example, CTNNB1 targeting oligonucleotides made be found in International Patent Application PCT/US2011/042820, filed on Jul. 1, 2011; International Patent Publication Number WO 2012/018754, which was published on Feb. 9, 2012; and International Patent Publication Number WO 2013/105022, which was published on Jul. 18, 2013, the contents of each of which pertaining to CTNNB1 targeting oligonucleotides are hereby incorporated by reference in their entireties for this purpose.

Targeting sequences can be put into multiple different oligonucleotide structures (or formats) as described herein.

Accordingly, in some embodiments, oligonucleotides provided herein are designed so as to have regions of complementarity to CTNNB1 mRNA for purposes of targeting the mRNA in cells and inhibiting its expression. The region of complementarity is generally of a suitable length and base content to enable annealing of the oligonucleotide (or a strand thereof) to CTNNB1 mRNA for purposes of inhibiting its expression.

In some embodiments, an oligonucleotide disclosed herein comprises a region of complementarity (e.g., on an antisense strand of a double-stranded oligonucleotide) that is at least partially complementary along its length to a sequence as set forth in SEQ ID NO: 3. In some embodiments, an oligonucleotide disclosed herein comprises a region of complementarity (e.g., on an antisense strand of a double-stranded oligonucleotide) that is fully complementary along its length to a sequence as set forth in SEQ ID NO: 3. In some embodiments, a region of complementarity of an oligonucleotide that is complementary to contiguous nucleotides of a sequence as set forth in SEQ ID NO: 3 spans the entire length of an antisense strand. In some embodiments, a region of complementarity of an oligonucleotide that is complementary to contiguous nucleotides of a sequence as set forth in any one of SEQ ID NO: 3 spans a portion of the entire length of an antisense strand (e.g., all but two nucleotides at the 3' end of the antisense strand).

In some embodiments, the region of complementarity is at least 12, at least 13, at least 14, at least 15, at least 16, at least 17, at least 18, at least 19, at least 20, at least 21, at least 22, at least 23, at least 24, at least 25 nucleotides in length. In some embodiments, an oligonucleotide provided herein has a region of complementarity to CTNNB1 that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to CTNNB1 that is 12, 13, 14, 15, 16, 17, 18, 19, 20, 21, 22, 23, 24, 25, 26, 27, 28, 29 or 30 nucleotides in length.

In some embodiments, a region of complementarity to CTNNB1 may have one or more mismatches compared with a corresponding sequence of CTNNB1 mRNA. A region of complementarity on an oligonucleotide may have up to 1, up to 2, up to 3, up to 4, up to 5, etc. mismatches provided that it maintains the ability to form complementary base pairs with CTNNB1 mRNA under appropriate hybridization conditions. Alternatively, a region of complementarity on an oligonucleotide may have no more than 1, no more than 2, no more than 3, no more than 4, or no more than 5 mismatches provided that it maintains the ability to form complementary base pairs with CTNNB1 mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with CTNNB1 mRNA under appropriate hybridization conditions.

ii. Oligonucleotide Structures

There are a variety of structures of oligonucleotides that are useful for targeting CTNNB1 mRNA in the methods of the present disclosure, including RNAi, miRNA, etc. Any of the structures described herein or elsewhere may be used as a framework to target CTNNB1 mRNA. Double-stranded oligonucleotides for targeting CTNNB1 expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked.

In some embodiments, double-stranded oligonucleotides for reducing expression of CTNNB1 engage RNA interference (RNAi). For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by Dicer to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, sequences described herein can be incorporated into, or targeted using, oligonucleotides that comprise sense and antisense strands that are both in the range of 17 to 36 nucleotides in length. In some embodiments, oligonucleotides incorporating such sequences are provided that have a tetraloop structure within a 3' extension of their sense strand, and two terminal overhang nucleotides at the 3' end of its antisense strand. In some embodiments, the two terminal overhang nucleotides are GG. Typically, one or both of the two terminal GG nucleotides of the antisense strand is or are not complementary to the target.

In some embodiments, oligonucleotides incorporating such sequences are provided that have sense and antisense strands that are both in the range of 21 to 23 nucleotides in length. In some embodiments, a 3' overhang is provided on the sense, antisense, or both sense and antisense strands that is 1 or 2 nucleotides in length. In some embodiments, an oligonucleotide has a guide strand of 23 nucleotides and a passenger strand of 21 nucleotides, in which the 3'-end of passenger strand and 5'-end of guide strand form a blunt end and where the guide strand has a two nucleotide 3' overhang.

In some embodiments, oligonucleotides may be in the range of 21 to 23 nucleotides in length. In some embodiments, oligonucleotides may have an overhang (e.g., of 1, 2, or 3 nucleotides in length) in the 3' end of the sense and/or antisense strands. In some embodiments, oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. See, for example, U.S. Pat. Nos. 9,012,138, 9,012,621, and 9,193,753, the contents of each of which are incorporated herein for their relevant disclosures.

In some embodiments, an oligonucleotide of the invention has a 36 nucleotide sense strand that comprises an region extending beyond the antisense-sense duplex, where the extension region has a stem-tetraloop structure where the stem is a six base pair duplex and where the tetraloop has four nucleotides. In certain of those embodiments, three or four of the tetraloop nucleotides are each conjugated to a monovalent GalNac ligand.

In some embodiments, an oligonucleotide of the invention comprises a 25 nucleotide sense strand and a 27 nucleotide antisense strand that when acted upon by a dicer enzyme results in an antisense strand that is incorporated into the mature RISC. [[Insert a reference that refers to this structure—don't hold up the filing]].

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p 163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p 193-198), single-stranded siRNAs (Elsner; Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of CTNNB1 are microRNA (miRNA), short hairpin RNA (shRNA), and short siRNA (see, e.g., Hamilton et al., Embo J., 2002, 21(17): 4671-4679; see also U.S. Application No. 20090099115).

a. Antisense Strands

In some embodiments, a double-stranded oligonucleotide may have an antisense strand of up to 40 nucleotides in length (e.g., up to 40, up to 35, up to 30, up to 27, up to 25, up to 21, up to 19, up to 17, or up to 12 nucleotides in length). In some embodiments, an oligonucleotide may have an antisense strand of at least 12 nucleotides in length (e.g., at least 12, at least 15, at least 19, at least 21, at least 22, at least 25, at least 27, at least 30, at least 35, or at least 38 nucleotides in length). In some embodiments, an oligonucleotide may have an antisense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments, a sense strand complementary to a guide strand may be referred to as a "passenger strand."

b. Sense Strands

In some embodiments, an oligonucleotide may have a sense strand (or passenger strand) of up to 40 nucleotides in length (e.g., up to 40, up to 36, up to 30, up to 27, up to 25, up to 21, up to 19, up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 36, or at least 38 nucleotides in length). In some embodiments, an oligonucleotide may have a sense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, a sense strand comprises a stem-loop structure at its 3'-end. In some embodiments, a sense strand comprises a stem-loop structure at its 5'-end. In some embodiments, a stem is a duplex of 2, 3, 4, 5, 6, 7, 8, 9, 10, 11, 12, 13, or 14 base pairs in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 3, 4, 5, 6, 7, 8, 9, or 10 nucleotides in length).

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides.

c. Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

d. Oligonucleotide Ends

In some embodiments, an oligonucleotide provided herein comprises sense and antisense strands, such that there is a 3'-overhang on either the sense strand or the antisense strand, or both the sense and antisense strand. In some embodiments, oligonucleotides provided herein have one 5'end that is thermodynamically less stable compared to the other 5' end. In some embodiments, an asymmetric oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7 or 8 nucleotides in length).

Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, one or more (e.g., 2, 3, 4) terminal nucleotides of the 3' end or 5' end of a sense and/or antisense strand are modified. For example, in some embodiments, one or two terminal nucleotides of the 3' end of an antisense strand are modified. In some embodiments, the last nucleotide at the 3' end of an antisense strand is modified, e.g., comprises 2'-modification, e.g., a 2'-O-methoxyethyl. In some embodiments, the last one or two terminal nucleotides at the 3' end of an antisense strand are complementary to the target. In some embodiments, the last one or two nucleotides at the 3' end of the antisense strand are not complementary to the target. In some embodiments, the 5' end and/or the 3' end of a sense or antisense strand has an inverted cap nucleotide.

e. Mismatches

In some embodiments, there is one or more (e.g., 1, 2, 3, 4, 5) mismatches between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

iii. Single-Stranded Oligonucleotides

In some embodiments, an oligonucleotide for reducing CTNNB1 expression as described herein is single-stranded. Such structures may include, but are not limited to single-stranded RNAi oligonucleotides. Recent efforts have demonstrated the activity of single-stranded RNAi oligonucleotides (see, e.g., Matsui et al. (May 2016), Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier (e.g., "naked delivery"), it may be advantageous for at least some of the its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every nucleotide is modified at the 2'-position of the sugar group of that nucleotide. These modifications may be reversible or irreversible. Typically, the 2'-position modification is 2'-fluoro, 2'-O-methyl, etc. In some embodiments, an oligonucleotide as disclosed herein has a number and type of modified nucleotides sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred to herein as a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659). Koshkin et al., Snead et al., and Imanishi and Obika are incorporated by reference herein for their disclosures relating to sugar modifications.

In some embodiments, a nucleotide modification in a sugar comprises a 2'-modification. In certain embodiments, the 2'-modification may be 2'-aminoethyl, 2'-fluoro, 2'-O-methyl, 2'-O-methoxyethyl, or 2'-deoxy-2'-fluoro-β-d-arabinonucleic acid. Typically, the modification is 2'-fluoro, 2'-O-methyl, or 2'-O-methoxyethyl. However, a large variety of 2' position modifications that have been developed for use in oligonucleotides can be employed in oligonucleotides disclosed herein. See, e.g., Bramsen et al., Nucleic Acids Res., 2009, 37, 2867-2881. In some embodiments, a modification in a sugar comprises a modification of the sugar ring, which may comprise modification of one or more carbons of the sugar ring. For example, a modification of a sugar of a nucleotide may comprise a linkage between the 2'-carbon and a 1'-carbon or 4'-carbon of the sugar. For example, the linkage may comprise an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) is a phosphate group or other group, which can be used, for example, to attach linkers, adapters or labels or for the direct ligation of an oligonucleotide to another nucleic acid.

b. 5' Terminal Phosphates

5'-terminal phosphate groups of oligonucleotides may or in some circumstances enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to a chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, International Patent Application PCT/US2017/049909, filed on Sep. 1, 2017, U.S. Provisional Application Nos. 62/383,207, entitled 4'-Phosphate Analogs and Oligonucleotides Comprising the Same, filed on Sep. 2, 2016, and 62/393,401, filed on Sep. 12, 2016, entitled 4'-Phosphate Analogs and Oligonucleotides Comprising the Same, the contents of each of which relating to phosphate analogs are incorporated herein by reference. In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—CH$_2$—PO(OH)$_2$ or —O—CH$_2$—PO(OR)$_2$, in which R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$, or a protecting group. In certain embodiments, the alkyl group is CH$_2$CH$_3$. More typically, R is independently selected from H, CH$_3$, or CH$_2$CH$_3$.

c. Modified Internucleoside Linkages

In some embodiments, the oligonucleotide may comprise a modified internucleoside linkage. In some embodiments, phosphate modifications or substitutions may result in an oligonucleotide that comprises at least one (e.g., at least 1, at least 2, at least 3 or at least 5) modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorodithioate linkage, a phosphorothioate linkage, a phosphotriester linkage, a thionoalkylphosphonate linkage, a thionoalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

d. Base Modifications

In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain a nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution that, when present in a duplex, can be positioned opposite more than one type of base without substantially altering the structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., Nature Biotechnology, 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. J. Am. Chem. Soc. 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of a sugar, particularly when the modified nucleotide is the 3'-terminal nucleotide of the oligonucleotide. In some embodiments, the glutathione-sensitive moiety comprises a sulfonyl group. See, e.g., International Patent Application Publication WO 2018/039364, which was published on Mar. 1, 2018, and U.S. Prov. Appl. No. 62/378,635, entitled Compositions Comprising Reversibly Modified Oligonucleotides and Uses Thereof, which was filed on Aug. 23, 2016, the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligands.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferrin, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a targeting ligand, as described, for example, in International Patent Application Publication WO 2016/100401, which was published on Jun. 23, 2016, the relevant contents of which are incorporated herein by reference.

In some embodiments, it is desirable to target an oligonucleotide that reduces the expression of CTNNB1 to the hepatocytes of the liver of a subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to one or more bivalent GalNAc, trivalent GalNAc, or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand, where each GalNAc moiety is conjugated to one nucleotide.

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable. In some embodiments, a duplex extension (up to 3, 4, 5, or 6 base pairs in length) is provided between a targeting ligand (e.g., a GalNAc moiety) and a double-stranded oligonucleotide.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of CTNNB1. Such compositions can be suitably formulated such that when administered to a subject, either into the immediate environment of a target cell or systemically, a sufficient portion of the oligonucleotides enter the cell to reduce CTNNB1 expression. Any of a variety of suitable oligonucleotide formulations can be used to deliver oligonucleotides for the reduction of CTNNB1 as disclosed herein. In some embodiments, an oligonucleotide is formulated in buffer solutions such as phosphate-buffered saline solutions, liposomes, micellar structures, and capsids. In some embodiments, naked oligonucleotides or conjugates thereof are formulated in water or in an aqueous solution (e.g., water with pH adjustments). In some embodiments, naked oligonucleotides or conjugates thereof are formulated in basic buffered aqueous solutions (e.g., PBS)

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Typically. the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. For intravenous or subcutaneous administration, suitable carriers include physiological saline, bacteriostatic water, Cremophor EL.TM. (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., an oligonucleotide for reducing CTNNB1 expression) or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing CTNNB1 Expression in Cells

In some embodiments, methods are provided for delivering to a cell an effective amount any one of oligonucleotides disclosed herein for purposes of reducing expression of CTNNB1 in the cell. Methods provided herein are useful in any appropriate cell type. In some embodiments, a cell is any cell that expresses CTNNB1 (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue and skin). In some embodiments, the cell is a primary cell that has been obtained from a subject and that may have undergone a limited number of a passages, such that the cell substantially maintains its natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of CTNNB1 solely in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of CTNNB1 expression (e.g., RNA, protein). In some embodiments, the extent to which an oligonucleotide provided herein reduces levels of expression of CTNNB1 is evaluated by comparing expression levels (e.g., mRNA or protein levels of CTNNB1 to an appropriate control (e.g., a level of CTNNB1 expression in a cell or population of cells to which an oligonucleotide has not been delivered or to which a negative control has been delivered). In some embodiments, an appropriate control level of CTNNB1 expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of CTNNB1 expression in a cell. In some embodiments, the reduction in levels of CTNNB1 expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of CTNNB1. The appropriate control level may be a level of CTNNB1 expression in a cell or population of cells that has not been contacted with an oligonucleotide as described herein. In some embodiments, the effect of delivery of an oligonucleotide to a cell according to a method disclosed herein is assessed after a finite period of time. For example, levels of CTNNB1 may be analyzed in a cell at least 8 hours, 12 hours, 18 hours, 24 hours; or at least one, two, three, four, five, six, seven, or fourteen days after introduction of the oligonucleotide into the cell.

In some embodiments, an oligonucleotide is delivered in the form of a transgene that is engineered to express in a cell the oligonucleotides (e.g., its sense and antisense strands). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing CTNNB1 expression for the treatment of bile duct paucity in a subject. In some embodiments, the methods may comprise administering to a subject in need thereof an effective amount of any one of the oligonucleotides disclosed herein. Such treatments could be used, for example, to promote bile duct and/or regeneration in a subject, thereby promoting draining of bile acid. The treatments could also be used, for example, in inhibiting bile acid synthesis in a subject, thereby reducing liver damage. The present disclosure provides for both prophylactic and therapeutic methods of treating a subject at risk of (or susceptible to) bile duct paucity and/or a disease or disorder associated with bile duct paucity (e.g., including Alagille syndrome and Biliary Atresia).

In certain aspects, the disclosure provides a method for preventing in a subject, a disease or disorder as described herein by administering to the subject a therapeutic agent (e.g., an oligonucleotide or vector or transgene encoding same). In some embodiments, the subject to be treated is a subject who will benefit therapeutically from a reduction in the amount of β-catenin protein, e.g., in the liver.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intramuscular injection,), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

In some embodiments, oligonucleotides are administered at a dose in a range of 0.1 mg/kg to 25 mg/kg (e.g., 1 mg/kg to 5 mg/kg). In some embodiments, oligonucleotides are administered at a dose in a range of 0.1 mg/kg to 5 mg/kg or in a range of 0.5 mg/kg to 5 mg/kg.

As a non-limiting set of examples, the oligonucleotides of the instant disclosure would typically be administered once per year, twice per year, quarterly (once every three months), bi-monthly (once every two months), monthly, or weekly.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Figure 2:
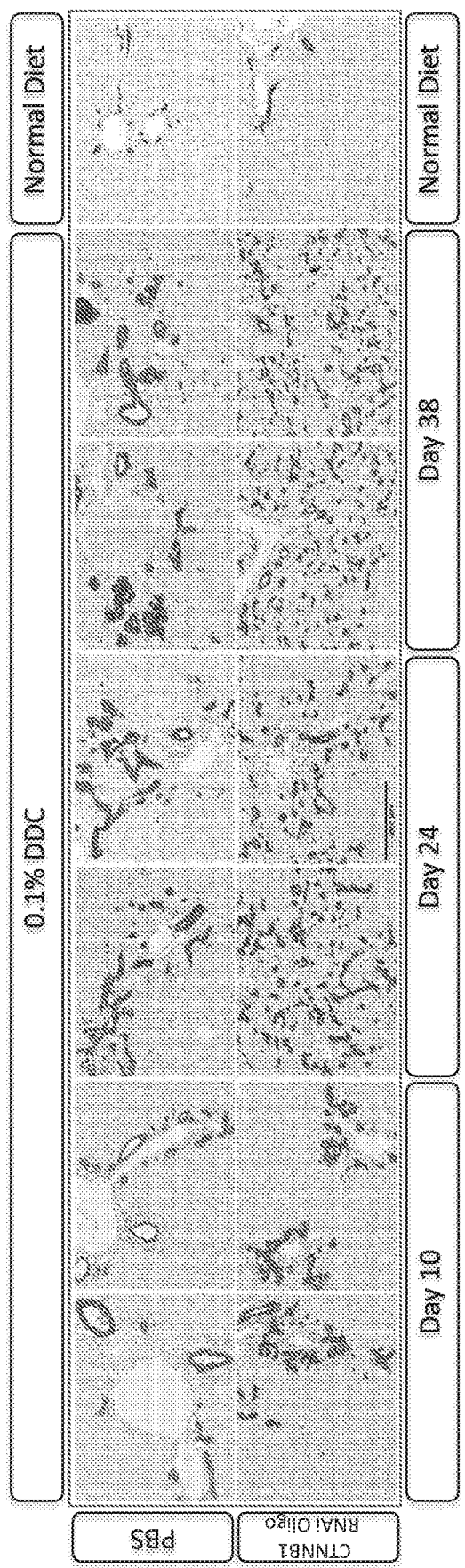
FIG. 2 includes a series of photographs showing immunohistochemistry staining for CK19 in liver sections from mice fed 0.1% DDC and treated with PBS or CTNNB1 RNAi oligonucleotide weekly for 10 days, 24 days, or 38 days. The top row of photographs show results with PBS treatment and the bottom row of photographs shows results with CTNNB1 RNAi oligonucleotide. The treatment day is shown on the bottom with two immunohistochemistry stains for each day. Results for mice on a normal diet (mice not fed 0.1% DDC) for each treatment are shown on the far right.
Figure 5:
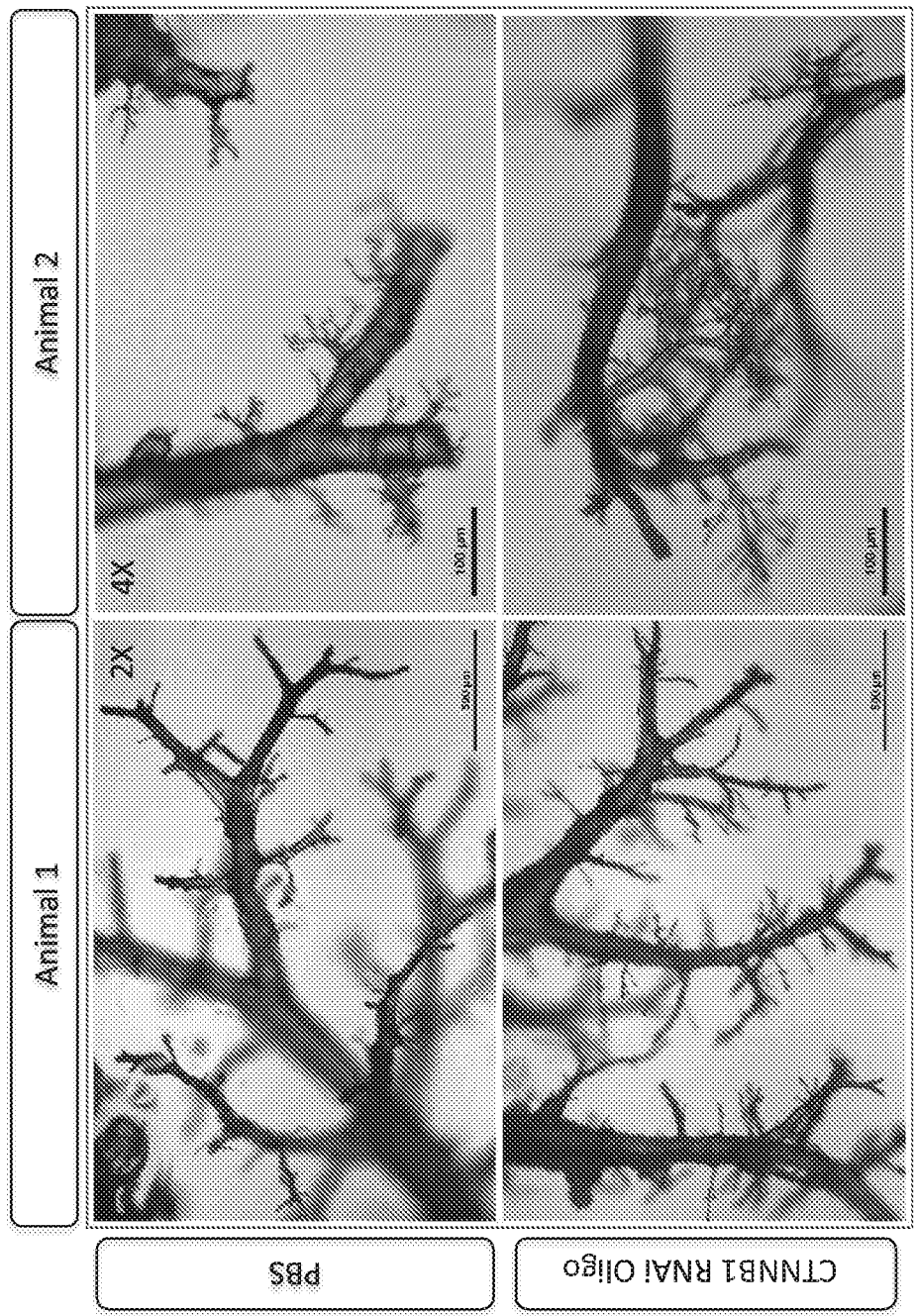
FIG. 5 is a series of photographs showing ductule architecture using resin casting in two DDC-fed animals (Animal 1 and Animal 2) treated with PBS (top two panels) or with CTNNB1 RNAi oligonucleotide (bottom two panels). The images for Animal 1 are with 2× magnification with the scale bars indicating 500 μm and the images for Animal 2 are with 4× magnification with the scale bars indicating 100 μm.

Example 1: Evaluation of CTNNB1 RNAi Oligonucleotide Treatment in a 3,5-diethoxycarbonyl-1,4-dihydrocollidine (DDC)-Fed Mouse Model of Bile Duct Damage To determine the effect of targeting CTNNB1 on bile epithelial cell differentiation, Swiss Webster mice were fed 0.1% 3,5-diethoxycarbonyl-1,4-dihydrocollidine (DDC) and treated with a CTNNB1 RNAi oligonucleotide (having a sense strand sequence as set forth in SEQ ID NO: 1 and an antisense strand sequence as set forth in SEQ ID NO: 2). The RNAi oligonucleotide contained a nicked tetraloop structure, including single monovalent GalNac moieties conjugated at each of four nucleotides of the tetraloop (-GAAA-) on its sense strand and a phosphate analog at the 5' end of its antisense strand. As a control, DDC-fed mice were treated with PBS. Immunohistochemistry staining was performed on liver sections from DDC-fed mice treated with PBS or CTNNB1 RNAi oligonucleotide using a rabbit monoclonal antibody (catalog number: ab52625, Abcam, Cambridge, Mass.) against the ductal epithelial marker CK19 (FIG. 1 and FIG. 2). In FIG. 2, liver sections from mice on a normal diet treated with PBS or CTNNB1 RNAi oligonucleotides were also evaluated. Mice were dosed weekly (days 0, 7, 14, 21, 28, 35) and sacrificed 3 days post-dose as indicated in FIG. 2. Resin casting was used to visualize ductule architecture in DDC-fed mice treated with control PBS or with CTNNB1 RNAi oligonucleotide (FIG. 5).

Figure 6:
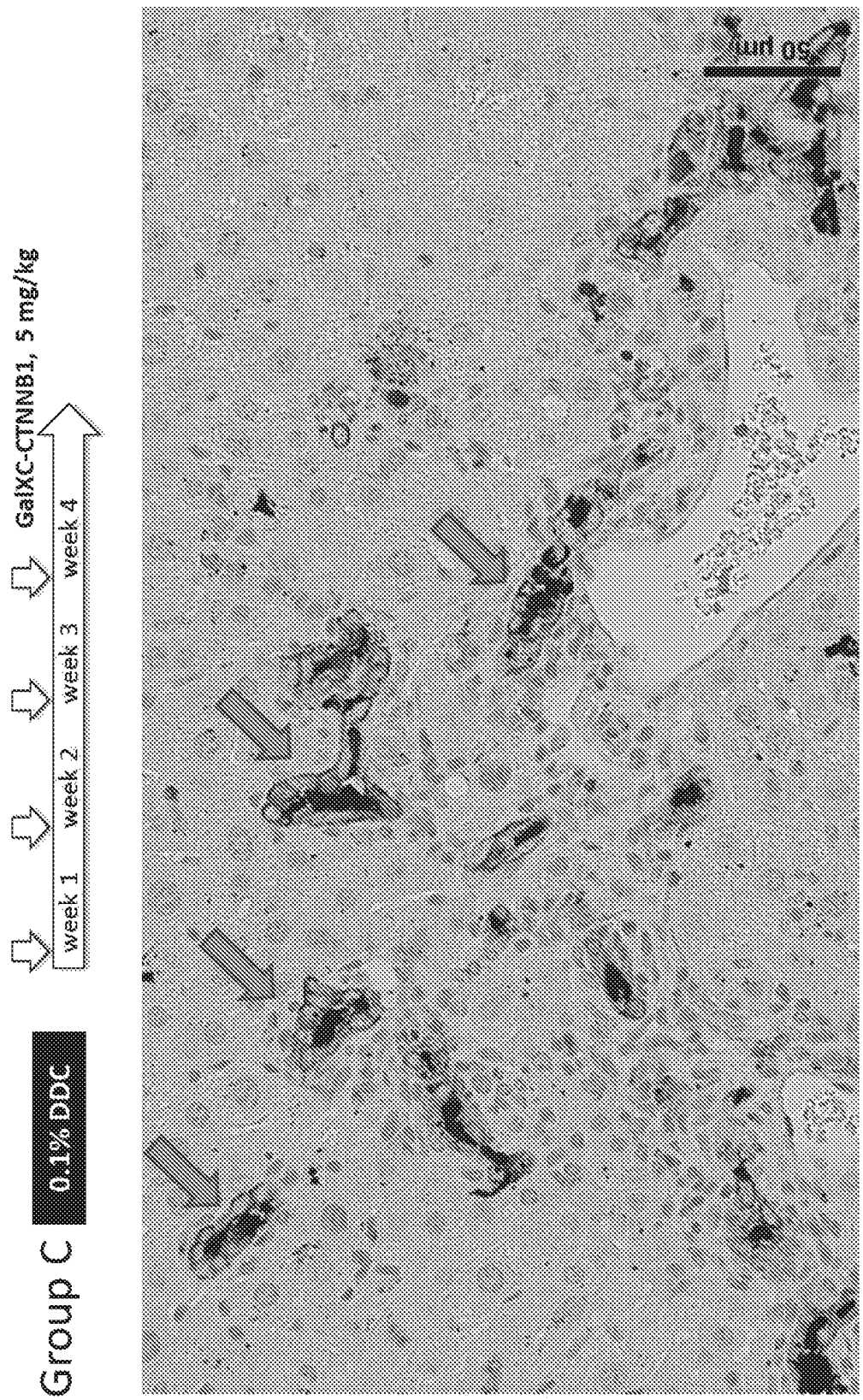
FIG. 6 is a photograph showing ductule architecture by ink injection in a single DDC-fed animal treated with CTNNB1 RNAi oligonucleotide. The images are with 10× magnification with the scale bars indicating 50 μm.

As shown in FIG. 1, liver sections from DDC-fed mice treated with CTNNB1 RNAi oligonucleotide (having a sense strand sequence as set forth in SEQ ID NO: 1 and an antisense strand sequence as set forth in SEQ ID NO: 2) for 24 days had increased numbers of CK19 positive cells compared to control DDC-mice treated with PBS. Similar results were found in a time course study shown in FIG. 2. DDC-feeding results in an increase in the number of CK19 staining that is further increased in liver sections from DCC-fed mice treated with CTNNB1 RNAi oligonucleotide (having a sense strand sequence as set forth in SEQ ID NO: 1 and an antisense strand sequence as set forth in SEQ ID NO: 2) compared to liver sections from DDC-fed mice treated with PBS 10 days, 24 days and 38 days after the first dose of CTNNB1 RNAi oligonucleotides (FIG. 2). More small ductules were also observed in DDC-fed mice receiving CTNNB1 RNAi oligonucleotides compared to mice receiving control PBS (FIG. 5). Furthermore, new small bile ductules are fully formed and connected to the biliary system as evidenced by the co-localization of CK19 positively-stained cells and ink injected into the common bile duct in DDC-fed mice treated with CTNNB1 RNAi oligonucleotide (FIG. 6). Therefore, the results suggest that RNAi oligonucleotide targeting of CTNNB1 mRNA induces bile epithelial cell differentiation and promotes bile duct regeneration in a DDC-fed mouse model of hepatic injury.

Example 2: Evaluation of CTNNB1 RNAi Oligonucleotide Treatment in a Mdr2$^{-/-}$ Mouse Model of Bile Duct Damage CTNNB1 RNAi oligonucleotides (having a sense strand sequence as set forth in SEQ ID NO: 1 and an antisense strand sequence as set forth in SEQ ID NO: 2) were also tested in another mouse model of biliary damage (Mdr2$^{-/-}$ mice). Mdr2$^{-/-}$ mice were treated with PBS or CTNNB1

RNAi oligonucleotides for 66 days. Liver sections from treated mice were stained for the ductal epithelial marker CK19. A liver section from a Mdr2$^{+/-}$ mouse treated with PBS was also analyzed.

Figure 3:
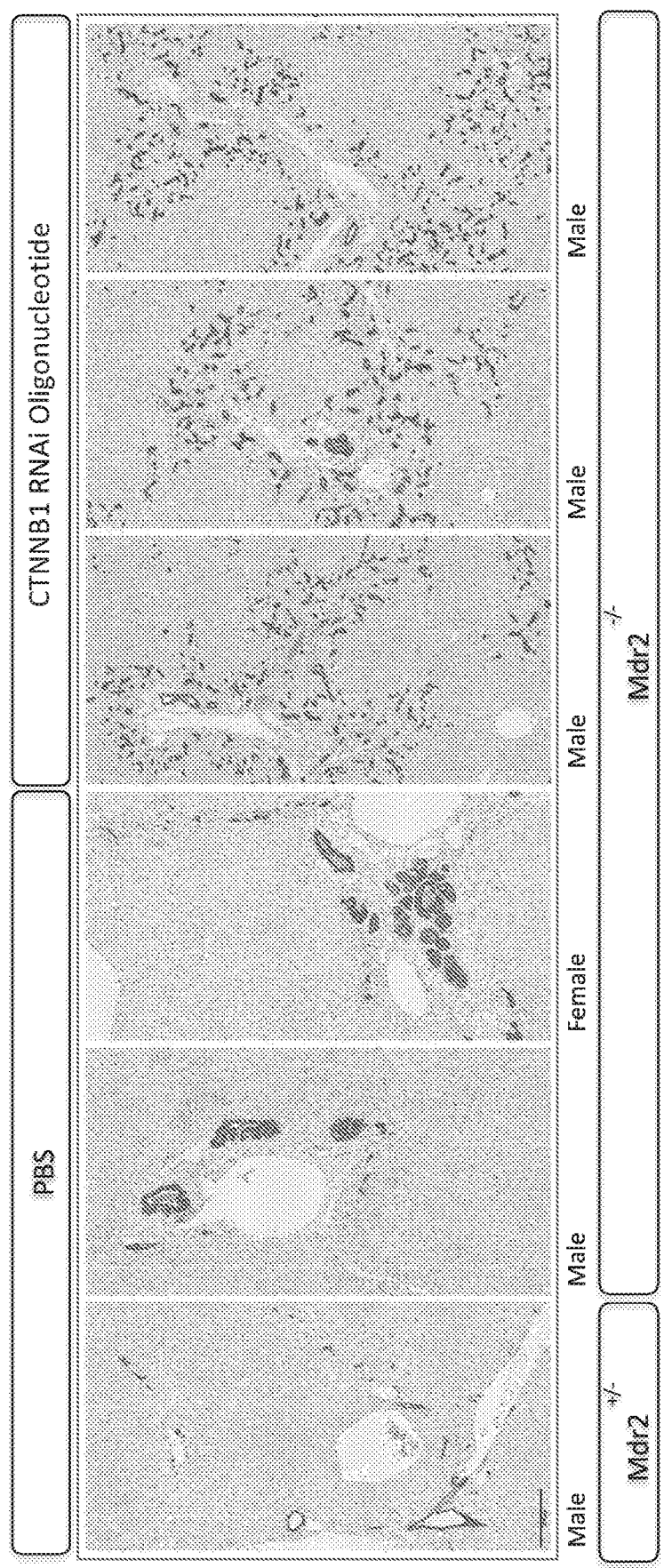
FIG. 3 is a series of photographs showing immunohistochemistry staining for CK19 in liver sections from Mdr2$^{+/-}$ mice treated with PBS (first panel at left), from Mdr$^{-/-}$ mice treated with PBS (second and third panels from left), and from Mdr$^{-/-}$ mice treated with CTNNB1 RNAi oligonucleotide (final three panels shown at right). The gender of each mouse is indicated below the relevant panel.

As shown in FIG. 3, Mdr2$^{-/-}$ mice have increased CK19 staining compared to Mdr2$^{+/-}$ mice. A further increase in the number of CK19 positive cells was detected in liver sections from Mdr2$^{-/-}$ mice treated with CTNNB1 RNAi oligonucleotide compared to Mdr2$^{-/-}$ mice treated with PBS. (FIG. 3). Therefore, CTNNB1 RNAi oligonucleotides also potentially induces bile epithelial cell differentiation in Mdr2$^{-/-}$ mice.

Example 3: Evaluation of CTNNB1 RNAi Oligonucleotide Treatment in Wildtype Mice Fed a Normal Diets The effect of targeting CTNNB1 on bile epithelial cell differentiation was also evaluated in wildtype mice. CD-1 mice were treated with control PBS, 10 mg/kg CTNNB1 RNAi oligonucleotide, or 100 mg/kg CTNNB1 RNAi oligonucleotide once weekly for six weeks (Q1W×6). Liver sections from treated animals were then stained with an antibody that recognizes the ductal epithelial marker CK19.

Figure 4:
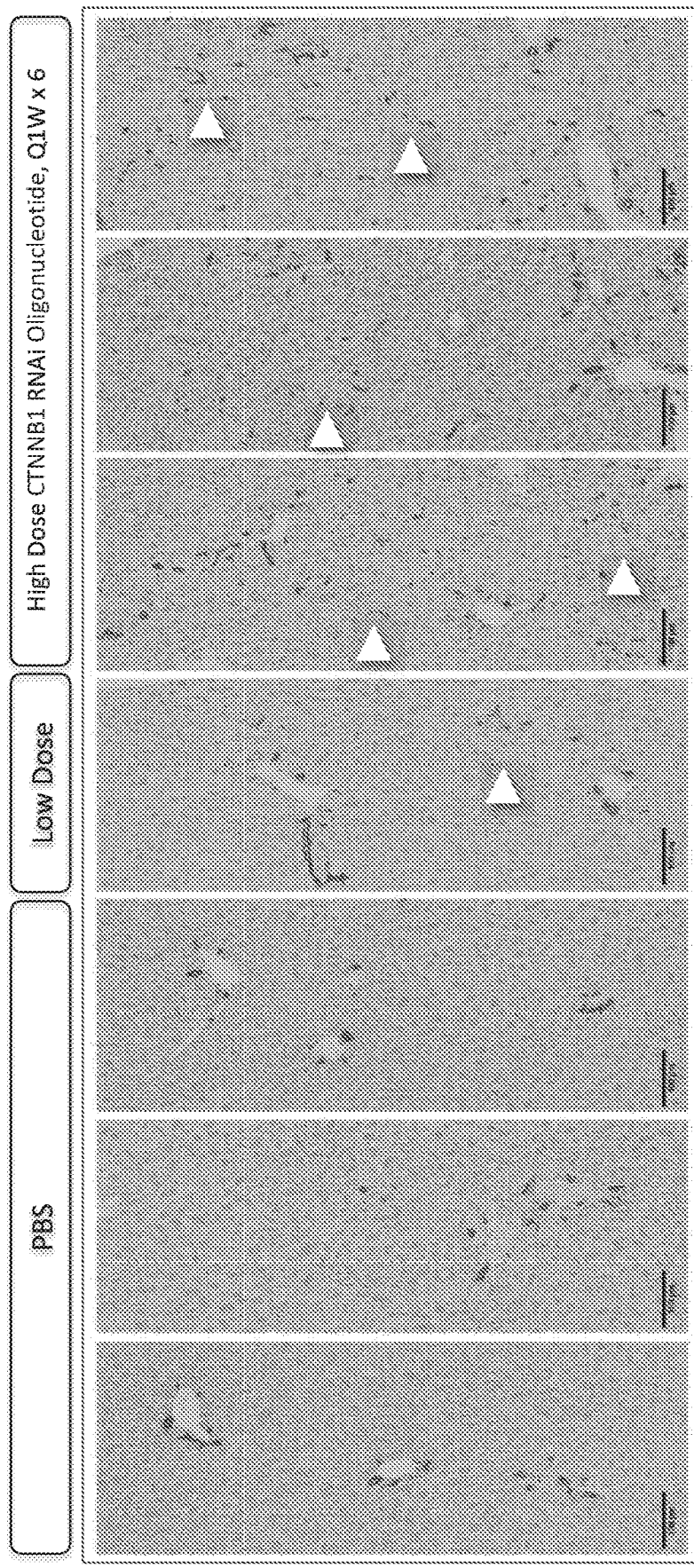
FIG. 4 is a series of photographs showing immunohistochemistry staining for CK19 in liver sections from each individual wildtype animal treated with PBS (first three panels starting at left), 5 mg/kg CTNNB1 RNAi oligonucleotide (fourth panel from left) and 100 mg/kg CTNNB1 RNAi oligonucleotide, Q1W×6 (last three panels shown at right). Arrows indicate areas having CK19 positive cells in non-periportal areas of the parenchymal compartment. The scale bar indicates 100 μm.

As shown in FIG. 4, increased numbers of CK19-positive cells were observed in liver sections from wildtype mice treated with 10 or 100 mg/kg CTNNB1 RNAi oligonucleotide compared to PBS-treated mice. These results indicate that RNA targeting of CTNNB1 mRNA potentially induces bile epithelial cell differentiation in wildtype mice.

Example 4: Evaluation of CTNNB1 RNAi Oligonucleotide Treatment on Bile Synthesis in a DDC Fed Mouse Model of Bile Duct Damage The effect of targeting CTNNB1 mRNA on bile synthesis was characterized in a DDC-fed mouse model of bile duct damage. Swiss Webster female mice were randomized into one of three treatment conditions. In the first group, mice were fed a control diet and treated with PBS. In the second group, mice were fed a 0.1% DDC diet and treated with PBS. In the third group, mice were fed a 0.1% DDC diet and treated with CTNNB1 RNAi oligonucleotide. The total bile acid concentration (FIG. 7A), the bile flow rate (FIG. 7B) and mRNA expression (FIG. 7C) in the liver were evaluated for each treatment group. In particular, the levels of CTNNB1, Cyp7a1, Cyp27a, Cyp8B1 and Shp mRNA were measured (FIG. 7C).

Figure 7A:
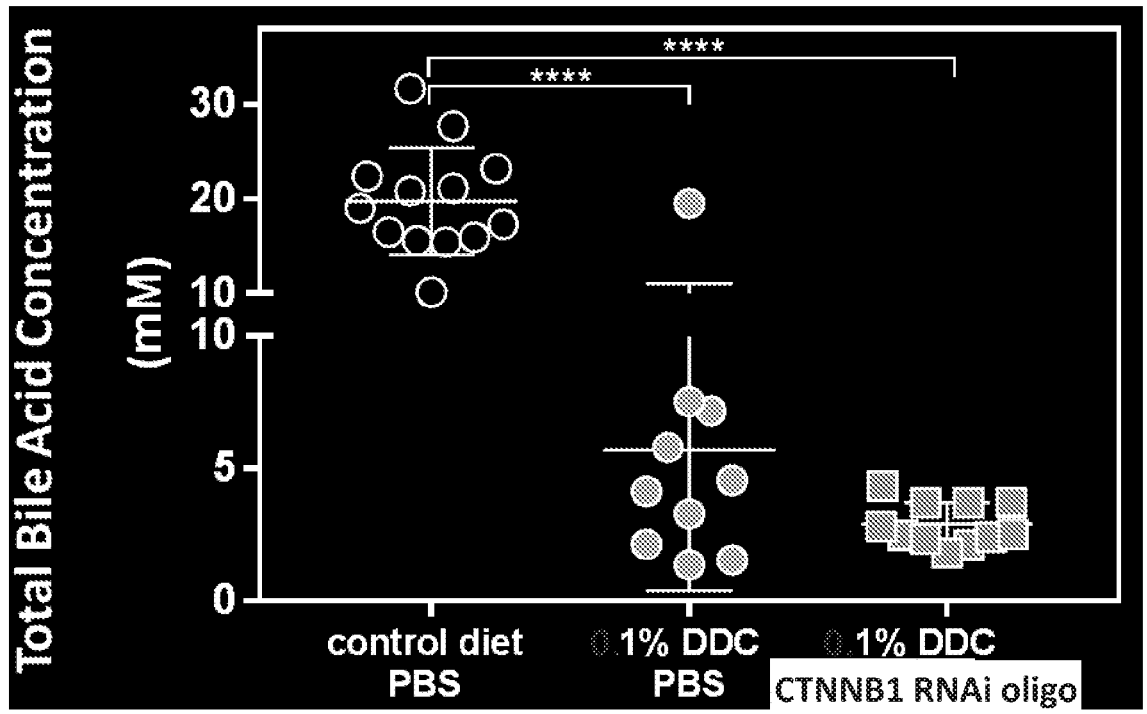
FIG. 7A is a graph comparing the total bile acid concentration from bile samples collected by gravity flow from mice on a control diet treated with PBS, fed 0.1% DDC and treated with PBS, and from mice fed 0.1% DDC while being treated with four weekly doses of CTNNB1 RNAi oligonucleotide. Swiss Webster female mice were used.
Figure 7B:
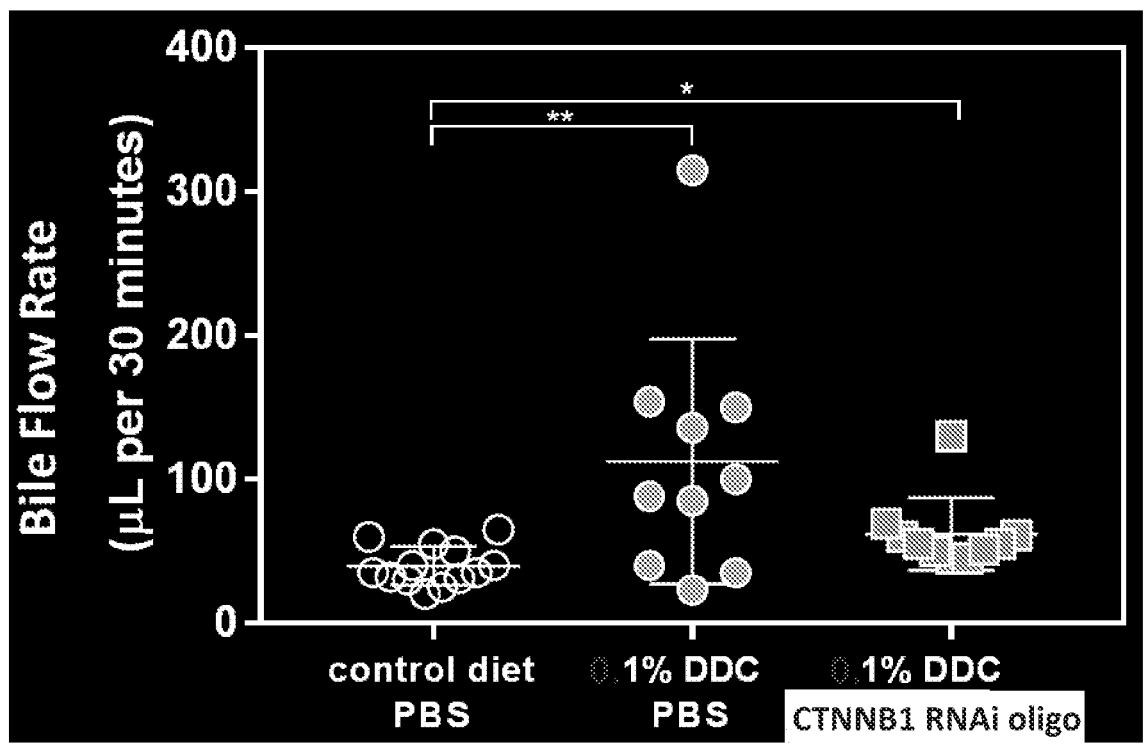
FIG. 7B is a graph comparing the bile flow rate for mice on a control diet treated with PBS, for mice fed 0.1% DDC treated with PBS and for mice fed 0.1% DDC treated QW×4 with CTNNB1 RNAi oligonucleotide. Swiss Webster female mice were used.
Figure 7C:
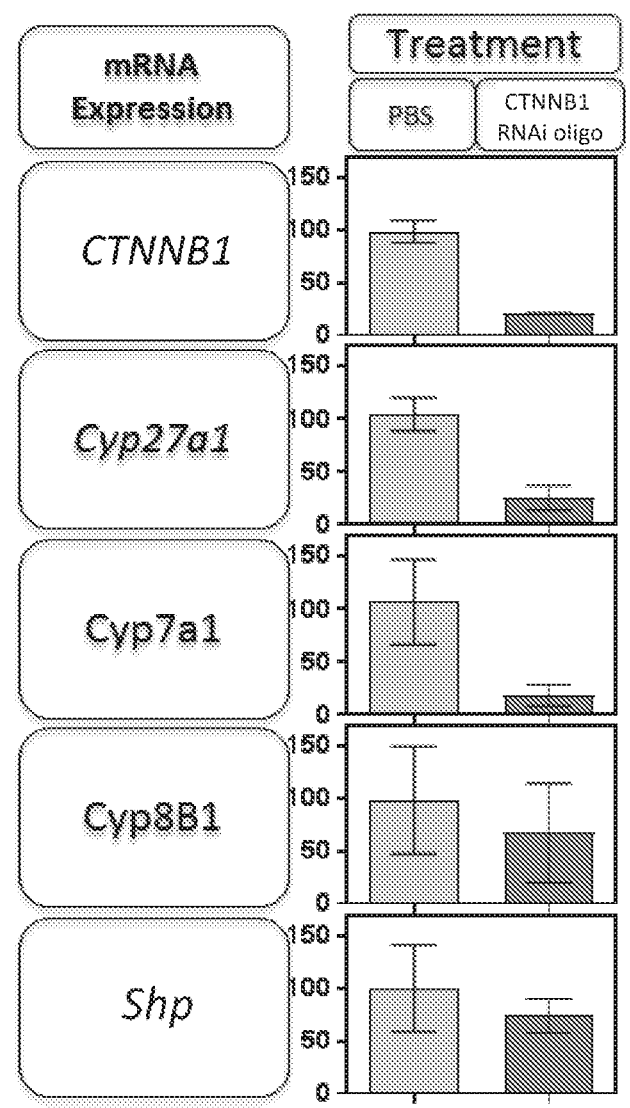
FIG. 7C is a series of graphs comparing expression of CTNNB1, Cyp27a1, Cyp7a1, Cyp8B1 and Shp in DDC-fed mice treated with PBS (light gray bars) and in mice treated QW×4 with CTNNB1 RNAi oligonucleotide (dark gray bars). Swiss Webster female mice were used.

As shown in FIG. 7A, DDC-fed mice treated with PBS or CTNNB1 RNAi oligonucleotides had lower bile acid concentrations compared to mice fed a control diet. A trend towards reduced total bile acid concentration was observed with CTNNB1 RNAi oligonucleotide treatment in DDC-fed mice. As shown in FIG. 7B, the bile flow rate was increased in DDC-fed mice compared to mice fed control diet. Treatment with β-catenin RNAi oligonucleotide partially normalized the DDC-feeding induced increase in bile flow rate. Notably, treatment of DDC-fed mice with CTNNB1 RNAi oligonucleotide reduced expression of Cyp7a1 and Cyp27a (FIG. 7C). These results indicate that CTNNB1 RNAi oligonucleotides reduces bile acid synthesis in a mouse model of bile duct damage.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A method of promoting bile duct formation in a subject in need thereof, the method comprising administering an oligonucleotide to the subject that reduces CTNNB1 expression, wherein the oligonucleotide comprises a sense strand having a sequence as set forth in SEQ ID NO: 1 and an antisense strand having a sequence as set forth in SEQ ID NO: 2.

2. The method of claim 1, wherein the administration results in an increase in the number and/or size of functional bile ducts in the subject.

3. The method of claim 1, wherein the administration results in an increase in the surface area of bile ducts in the subject.

4. The method of claim 1, wherein prior to administration of the oligonucleotide, the subject is identified as having a bile duct paucity (BDP)-associated condition.

5. The method of claim 4, wherein the BDP-associated condition is Alagille syndrome or Biliary Atresia.

6. The method of claim 5, wherein the BDP-associated condition is Type I Biliary Atresia, Type II Biliary Atresia, or Type III Biliary Atresia.

7. The method of claim 2, wherein the bile ducts of the subject are intrahepatic bile ducts.

8. The method of claim 2, wherein the bile ducts of the subject are extrahepatic bile ducts.

9. The method of claim 1, wherein the subject is an adolescent human subject.

10. The method of claim 1, wherein the oligonucleotide comprises at least one modified nucleotide.

11. The method of claim 10, wherein the modified nucleotide comprises a 2'-modification.

12. The method of claim 11, wherein the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid.

13. The method of claim 10, wherein all of the nucleotides of the oligonucleotide are modified.

14. The method of claim 1, wherein the oligonucleotide comprises at least one modified internucleotide linkage.

15. The method of claim 14, wherein the at least one modified internucleotide linkage is a phosphorothioate linkage.

16. The method of claim 1, wherein the 4'-carbon of the sugar of the 5'-nucleotide of the antisense strand comprises a phosphate analog.

17. The method of claim 16, wherein the phosphate analog is oxymethylphosphonate, vinylphosphonate, or malonylphosphonate.

18. The method of claim 1, wherein at least one nucleotide of the oligonucleotide is conjugated to one or more targeting ligands.

19. The method of claim 18, wherein each targeting ligand comprises a N-acetylgalactosamine (GalNAc) moiety.

20. The method of claim 19, wherein the GalNAc moiety is a monovalent GalNAc moiety, a bivalent GalNAc moiety, a trivalent GalNAc moiety, or a tetravalent GalNAc moiety.

21. The method of claim 18, wherein up to 4 nucleotides of the oligonucleotide are each conjugated to a monovalent GalNAc moiety.

22. The method of claim 11, wherein the 2'-modification is a modification selected from 2'-fluoro and 2'-O-methyl.

* * * * *